United States Patent [19]

Stalcup et al.

[11] Patent Number: 5,562,674
[45] Date of Patent: Oct. 8, 1996

[54] INTRAMEDULLARY ROD WITH GUIDE MEMBER LOCATOR

[75] Inventors: Gregory C. Stalcup, Columbia City; Steven E. Dietzel, Peru; Rodney Bays, Pierceton, all of Ind.

[73] Assignee: Zimmer, Inc., Warsaw, Ind.

[21] Appl. No.: 395,234

[22] Filed: Feb. 27, 1995

[51] Int. Cl.⁶ ............................ A61B 17/17; A61B 17/15
[52] U.S. Cl. ............................... 606/88; 606/87; 606/96
[58] Field of Search ................................ 606/79, 86, 87, 606/88, 89, 96, 97, 98, 162, 82

[56] References Cited

U.S. PATENT DOCUMENTS

| | | |
|---|---|---|
| 4,567,885 | 2/1986 | Androphy . |
| 4,646,729 | 3/1987 | Kenna et al. . |
| 4,703,751 | 11/1987 | Pohl . |
| 4,722,330 | 2/1988 | Russell et al. . |
| 4,736,737 | 4/1988 | Fargie et al. . |
| 4,738,253 | 4/1988 | Buechel et al. . |
| 4,738,254 | 4/1988 | Buechel et al. . |
| 4,759,350 | 7/1988 | Dunn et al. . |
| 4,773,407 | 9/1988 | Petersen . |
| 4,825,857 | 5/1989 | Kenna . |
| 4,935,023 | 6/1990 | Whiteside et al. ................ 606/88 |
| 4,952,213 | 8/1990 | Bowman et al. . |
| 5,002,545 | 3/1991 | Whiteside et al. ................ 606/80 |
| 5,037,423 | 8/1991 | Kenna ................................ 606/88 |
| 5,047,032 | 9/1991 | Jellicoe ............................. 606/83 |
| 5,053,037 | 10/1991 | Lackey ............................. 606/79 |
| 5,100,408 | 3/1992 | Lackey ............................. 606/79 |
| 5,282,803 | 2/1994 | Lackey ............................. 606/80 |
| 5,342,367 | 8/1994 | Ferrante et al. ................... 606/88 |
| 5,342,368 | 8/1994 | Petersen .......................... 606/88 |
| 5,417,694 | 5/1995 | Marik et al. ...................... 606/88 |
| 5,423,827 | 6/1995 | Mumme et al. ................... 606/96 |
| 5,484,446 | 1/1996 | Burke et al. ...................... 606/86 |

FOREIGN PATENT DOCUMENTS 0121142  10/1984  European Pat. Off. .

Primary Examiner—Michael P. Buiz
Assistant Examiner—Scott B. Markow
Attorney, Agent, or Firm—Todd A. Dawson

[57] ABSTRACT

The invention is directed to an intramedullary guide rod assembly for use in orthopaedic surgery for aligning one or more milling or cutting guides. A guide member is pivotally connected to an intramedullary guide rod intermediate and proximal and distal ends thereof. An alignment mechanism selectively locks the guide member to the intramedullary guide rod between discrete predetermined positions relative the guide rod.

3 Claims, 1 Drawing Sheet

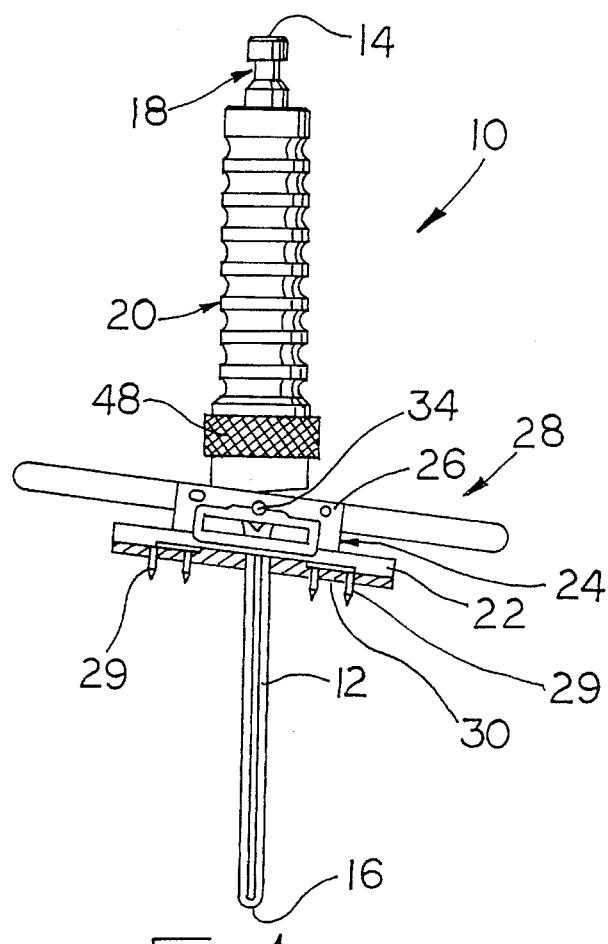
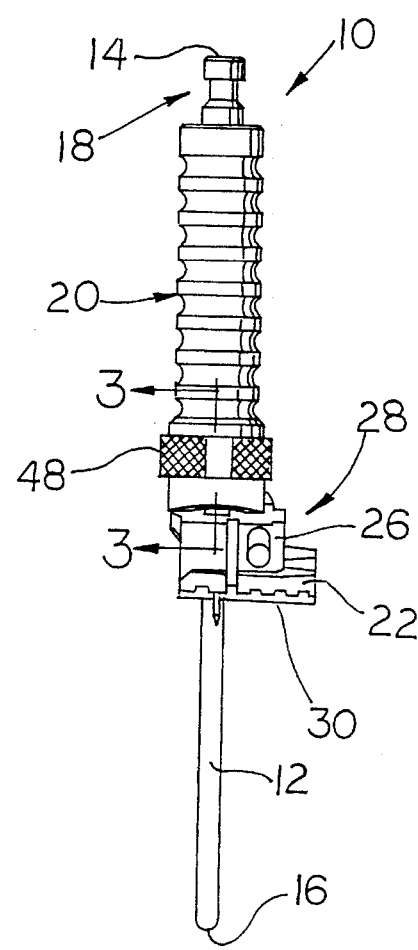
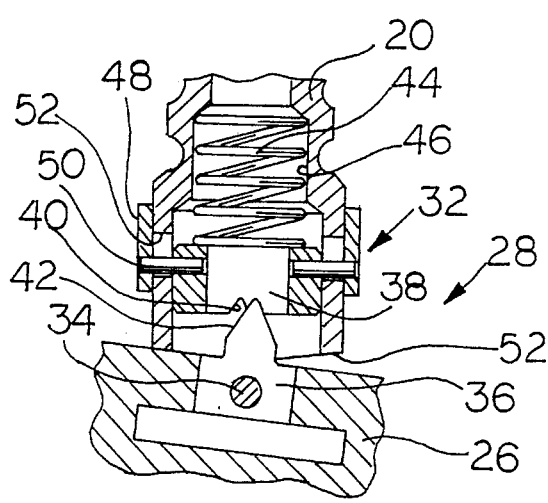
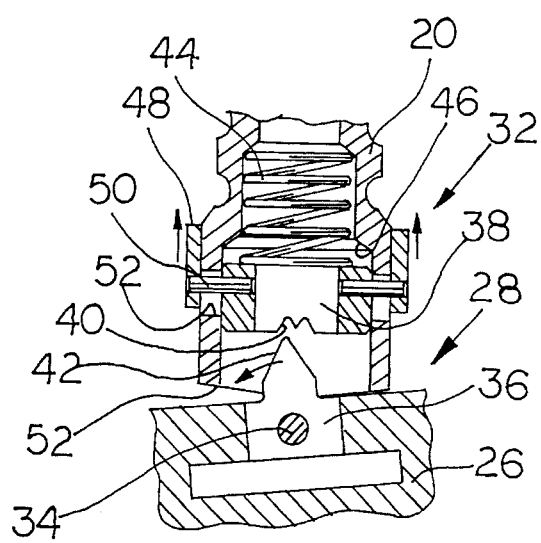

5,562,674

INTRAMEDULLARY ROD WITH GUIDE MEMBER LOCATOR

BACKGROUND OF THE INVENTION

1. Field of the Invention

The present invention relates to instrumentation used in orthopaedic surgery, and, more particularly, to instrumentation providing for the alignment of milling guides or other instrumentation used to prepare bone for receiving a prosthesis.

2. Description of the Related Art

In an orthopaedic surgery to replace part or all of a patient's joint with a prosthetic implant, a portion of the implant receiving bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

Depending on the type of femoral implant to be accommodated by the femur, and the particular side of body with which the implant is to be mated, there is a small set of angles to which the implant must be oriented relative to the mechanical axis of the bone. Typically, in the preparation of the femur, for example, one or more cutting guides are placed adjacent the distal femur in a specific order to resect portions of the femur in succession. These cutting guides are generally individually aligned by the surgeon with reference to specific anatomic landmarks.

What is needed in the art is an intramedullary rod with an attached guide mechanism to align the cutting or milling guides with a predetermined angle with the mechanical axis of the bone.

SUMMARY OF THE INVENTION

The present invention provides an intramedullary rod with a guide mechanism that aligns the guide member and other instruments to the bone receiving a prosthesis. The guide mechanism limits the alignment of the guide plate and other instruments to a discrete plurality of predetermined angles relative the intramedullary rod and therefore the bone.

The invention, in one form thereof, includes a biased toothed engagement member that releasably locks the guide member into a single position relative to the intramedullary rod, selected from a discrete plurality of possible positions.

An advantage of the intramedullary guide rod assembly of the present invention is that only predetermined angles between the guide member and intramedullary rod may be selected, thereby preventing misalignment of associated cutting or milling guides to the bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a front elevational view of one embodiment of the intramedullary rod of the present invention;

FIG. 2 is a side elevational view of the intramedullary rod shown in FIG. 1;

FIG. 3 is a sectional view of the intramedullary rod of FIG. 2, taken along line 3—3 and viewed in the direction of the arrows; and FIG. 4 is a sectional view of the intramedullary rod of FIG. 3, during pivotal movement of the guide member to a new discrete position.

Corresponding reference characters indicate corresponding pans throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings and particularly FIG. 1, an embodiment of an intramedullary guide rod assembly 10 of the present invention is shown. In general, intramedullary guide rod assembly 10 includes an intramedullary rod 12 having a distal end 14 and a proximal end 16. Distal end 14 includes a fitting or portion 18 for accommodating a gripping device for the removal of the intramedullary guide rod assembly 10 from a bone, such as the femur. A ridged handle 20 may be integrally formed or attached about the proximal portion of intramedullary rod 12 to assist the surgeon in manually gripping rod 12. Handle 20 also provides a housing for the locking mechanism.

Guide member 28, utilized for aligning milling and cutting guides to a bone, is located and pivotally attached to intramedullary rod 12 at a location which is intermediate distal end 14 and proximal end 16. A platform 22 is attached to guide member 28 and includes a pair of legs 24 extending therefrom and a base 26 as illustrated in FIG. 1. Base 26 includes a spacer 30 which may be selectively attached to base 26 by fasteners. Platform 22 and spacer 30 of guide member 28 both include central openings for accommodating intramedullary rod 12 therethrough. Spacer 30 or platform 22 may include extending pins 29 so that guide member 28 may be temporarily fixed to a bone. Guide member 28 is utilized for establishing a reference point relative to the bone to be resected by milling or cutting.

For further details of the milling and cutting alignment guides attachable to guide member 28, and use of an intramedullary rod, reference is made to co-pending U.S. patent application Ser. No. 08/169,459, now Pat. No. 5,474,559, which is hereby expressly incorporated herein by reference.

As depicted in FIG. 3, Guide member 28 is pivotally connected to intramedullary rod 12 by pivot 34. Pivot 34 would permit a wide continuum of relative angular positions between guide member 28 and intramedullary rod 12 if it were not for alignment mechanism 32.

Alignment mechanism 32 of the present invention, utilized for fixating and determining the relative angular position between guide member 28 and intramedullary rod 12 is most clearly shown in FIGS. 3 and 4. Alignment mechanism 32 includes a toothed member 36 connected to guide member 28 and a corresponding internally toothed catch member 38 slidably disposed within handle 20 and connected to intramedullary rod 12. Alternatively, the location and orientation of toothed members 36 and 38 may be reversed.

Internal teeth 40 of internally toothed catch member 38 create a plurality of discrete recesses into which tooth 42 of toothed member 36 may interfit. Normally, internally toothed catch member 38 is forced into a locking contact with tooth 42 by a biasing means, such as spring 44. Spring 44, along with internally toothed member 38, is disposed in a cavity 46 within handle 20. This biasing of internally toothed catch member 38 toward toothed member 36 causes guide member 28 to be locked into a predetermined position relative to intramedullary guide rod 12. These predetermined positions are discrete, formed by the recesses between internal teeth 40, such that only specific and predefined positions between guide member 28 and intramedullary rod 12 are able to be selectively chosen when spring 44 biases together toothed members 36 and 38.

To permit the relative angle between guide member 28 and intramedullary rod 12 to be changed, a retractor means, such as collar 48, is attached to internally toothed catch member 38 to permit a surgeon to retract toothed member 38 out of engagement with tooth 42. Collar 48 is attached to internally toothed member 38 via pins 50 disposed through openings 52 in handle 20.

In operation, alignment means 32 of the present invention enables a surgeon to select only predetermined, discrete positions between guide member 38 and intramedullary rod 12. The method of selectively locking guide member 28 to a predetermined relative position rod 12 requires that toothed members 36 and 38 become temporary unlocked and disengaged, while guide member 28 is pivoted about pivot 34 until tooth 42 is located into a position adjacent a different recess between internal teeth 40.

More particularly, the surgeon first grasps collar 48 and slides it along handle 20 in a direction away from toothed member 36, thereby pulling connected internally toothed catch member 38 away from toothed member 44. As collar 48 is moved, pins 50 slide through openings 52, causing attached catch member 38 to compress spring 46. When internally toothed catch member 38 is disengaged from toothed member 36, guide member 28 is free to rotate or pivot about pivot 34 to a new discrete, preselected position. After guide member 28 has been pivoted to the new desired position, collar 48 is released, permitting spring 44 to bias internally toothed catch member 38 back into engagement with tooth 42 of toothed member 36. The bias of spring 44 prevents relative pivotal movement between internally toothed catch member 38 and tooth 42, and between toothed member 36 and guide member 28, thereby locking guide member 28 into a selected position relative to intramedullary rod 12.

For additional stability during selection of the predetermined position of guide member 28, intramedullary rod 12 or handle 20 may include a shoulder 52 having at least two surfaces into which guide member 28 may engage when located in one of the discrete predetermined positions. Guide member 28 is pivotable into engagement with only one of the shoulder surfaces 52 at one time. Shoulder 52 thereby acts as a stop to restrain the pivoting of guide member 28.

The possible predetermined discrete positions of guide member 28 relative intramedullary rod 12 are determined by the interaction of tooth 42 with internal teeth 40. In the preferred embodiment of the invention, guide member 28 is permitted to locate to relative intramedullary rod 12 in a position either six (6) degrees left or right of the longitudinal axis of rod 12. These two angles are typical standard angles required to orient a prosthesis and establish a reference plane substantially perpendicular to the mechanical axis of a femur, for example, depending on whether it is a left or right side femur. Alternatively, other discrete and predetermined angles may be utilized without limitation.

While this invention has been described as having a preferred design, the present invention can be further modified within the spirit and scope of this disclosure. This application is therefore intended to cover any variations, uses, or adaptations of the invention using its general principles. Further this application is intended to cover such departures from the present disclosure as come within known or customary practice in the art to which this invention pertains and which fall within the limits of the appended claims.

What is claimed is:

1. An intramedullary instrument comprising, a rod having a proximal portion and a distal portion, the distal portion being adapted to extend into the intramedullary canal of a bone, the proximal portion of the rod includes a handle, a planar guide member pivotally connected to said rod by a pivot pin such that the guide member is pivotal about said pivot pin between first and second positions relative to said rod, alignment means carried on said rod between said proximal portion and said distal portion adjacent the handle and in contact with said planar guide member for selectively locking said planar guide member into one of said first and second positions, said planar guide member including a tooth for locking the guide member is one of the first and second positions by engaging one of the corresponding first and second notches on said alignment means, said alignment means being shiftable along said rod from a locking position wherein said tooth is positioned within one of the two notches of the alignment means to an unlocked position wherein said tooth is out of engagement with the notches and the alignment means and the planar guide member pivots freely about said pivot pin relative to the rod, said unlocked position being more proximally located on said rod relative to the locked position, said alignment means being biased toward said locked position.

2. The intramedullary instrument of claim 1 wherein said alignment means is generally cylindrical wherein said rod extends centrally through said alignment means.

3. The intramedullary instrument of claim 2 wherein said alignment means includes a grip portion about its periphery.

* * * * *